United States Patent
Chang et al.

(10) Patent No.: US 9,856,478 B2
(45) Date of Patent: Jan. 2, 2018

(54) METHOD FOR SELECTIVELY INHIBITING ACAT1 IN THE TREATMENT OF OBESITY, METABOLIC SYNDROME, AND ATHEROSCLEROSIS

(71) Applicant: Trustees of Dartmouth College, Hanover, NH (US)

(72) Inventors: Ta-Yuan Chang, Etna, NH (US); Catherine C. Y. Chang, Etna, NH (US); Li-Hao Huang, West Lebanon, NH (US); Elaina Melton, Hanover, NH (US); Paul Sohn, Las Vegas, NV (US)

(73) Assignee: TRUSTEES OF DARTMOUTH COLLEGE, Hanover, NH (US)

( * ) Notice: Subject to any disclaimer, the term of this patent is extended or adjusted under 35 U.S.C. 154(b) by 0 days.

(21) Appl. No.: 15/035,780

(22) PCT Filed: Sep. 10, 2014

(86) PCT No.: PCT/US2014/054917
§ 371 (c)(1),
(2) Date: May 11, 2016

(87) PCT Pub. No.: WO2015/065595
PCT Pub. Date: May 7, 2015

(65) Prior Publication Data
US 2016/0355824 A1     Dec. 8, 2016

Related U.S. Application Data

(60) Provisional application No. 61/897,318, filed on Oct. 30, 2013, provisional application No. 61/968,542, filed on Mar. 21, 2014.

(51) Int. Cl.
| | |
|---|---|
| *A61K 48/00* | (2006.01) |
| *C07H 21/02* | (2006.01) |
| *C07H 21/04* | (2006.01) |
| *C12N 15/113* | (2010.01) |
| *A61K 31/7105* | (2006.01) |
| *A61K 31/713* | (2006.01) |
| *A61K 9/127* | (2006.01) |
| *A01K 67/027* | (2006.01) |

(52) U.S. Cl.
CPC ...... *C12N 15/1137* (2013.01); *A01K 67/0271* (2013.01); *A61K 9/127* (2013.01); *A61K 31/713* (2013.01); *A61K 31/7105* (2013.01); *C12Y 203/01009* (2013.01); *A01K 2207/12* (2013.01); *A01K 2227/105* (2013.01); *A01K 2267/0362* (2013.01); *A01K 2267/0375* (2013.01); *C12N 2310/14* (2013.01); *C12N 2310/141* (2013.01); *C12N 2750/14143* (2013.01)

(58) Field of Classification Search
CPC ..... A61K 48/00; A61K 31/713; C12N 15/113
See application file for complete search history.

(56) References Cited

U.S. PATENT DOCUMENTS

| | | | |
|---|---|---|---|
| 6,121,283 A | 9/2000 | Chang et al. | 514/307 |
| 2003/0096773 A1 | 5/2003 | Crooke et al. | 514/44 |
| 2006/0257466 A1 | 11/2006 | Kim et al. | 424/450 |
| 2010/0291248 A1 | 11/2010 | Jeong et al. | 424/774 |
| 2011/0184173 A1 | 7/2011 | Tomoda et al. | 544/310 |
| 2013/0164364 A1 | 6/2013 | Paulson et al. | 424/450 |

FOREIGN PATENT DOCUMENTS

| | | |
|---|---|---|
| EP | 2228376 | 6/2015 |
| WO | WO03088962 | 10/2003 |
| WO | WO04111084 | 12/2004 |
| WO | WO06105666 | 10/2006 |
| WO | WO09081957 | 7/2009 |
| WO | WO13016315 | 1/2013 |

OTHER PUBLICATIONS

Weisberg et al. (J. Clin. Invest., 112, 1796-1808, 2003).*
Bocan et al. "The ACAT inhibitor avasimibe reduces macrophages and matrix metalloproteinase expression in atherosclerotic lesions of hypercholesterolemic rabbits" 2000 Arterioscler. Thromb. Vasc. Biol. 20(1):70-9.
Daugherty et al. "As macrophages indulge, atherosclerotic lesions bulge" 2008 Circ. Res. 102:1445-1447.
Hongo et al. "Leptin modulates ACAT1 expression and cholesterol efflux from human macrophages" 2009 Am. J. Physiol. Endocrinol. Metab. 297:E4'74-E482.
Huang et al. "Acat1 gene ablation in mice increases hematopoietic progenitor cell proliferation in bone marrow and causes leukocytosis" 2013 Arterioscler. Thromb. Vasc. Biol. 33:2081-2087.
Kusunoki et al. "Acyl-CoA:cholesterol acyltransferase inhibition reduces atherosclerosis in apolipoprotein E-deficient mice" 2001 Circulation 103(21):2604-9.
Lopez-Farre et al. "Inhibition of acyl-CoA cholesterol acyltransferase by F12511 (Eflucimibe): could it be a new antiatherosclerotic therapeutic?" 2008 Cardiovasc. Ther. 26:65-74.
Rival et al. "Anti-atherosclerotic properties of the acyl-coenzyme A:cholesterol acyltransferase inhibitor F 12511 in casein-fed New Zealand rabbits" 2002 J. Cardiovasc. Pharmacol. 39(2):181-91.
Rong et al. "ACAT inhibition reduces the progression of preexisting, advanced atherosclerotic mouse lesions without plaque or systemic toxicity" 2013. Arterioscler. Thromb. Vasc. Biol. 33:4-12.
Rudel et al. "ACAT2 is a target for treatment of coronary heart disease associated with hypercholesterolemia" 2005 Arterioscler. Thromb. Vasc. Biol. 25:1112-1118.
Stahlberg et al. "Hepatic cholesterol metabolism in human obesity" 1997 Hepatology 25:1447-1450.
Tomoda and Omura "Potential therapeutics for obesity and atherosclerosis: inhibitors of neutral lipid metabolism from microorganisms" 2007 Pharmacol. & Therapeut. 115:375-389.

(Continued)

*Primary Examiner* — Amy Bowman
(74) *Attorney, Agent, or Firm* — Licata & Tyrrell P.C.

(57) ABSTRACT

The present invention features methods for preventing and treating three related diseases, diet-induced obesity, metabolic syndrome, and atherosclerosis, alone or in combination by inhibiting Acyl-CoA:Cholesterol Acyltransferase 1 (ACAT1) activity or expression in myeloid cells.

5 Claims, No Drawings

(56) References Cited

OTHER PUBLICATIONS

Turkish and Sturley "Regulation of triglyceride metabolism. I. Eukaryotic neutral lipid synthesis: "Many ways to skin ACAT or a DGAT"" 2007 Am J. Physiol. Gastrointest. Liver Physiol. 292:G953-G957.
Xu et al. "MiR-9 reduces human acyl-coenzyme A:cholesterol acyltransferase-1 to decrease THP-1 macrophage-derived foam cell formation" 2013 Acta. Biochim. Biophys. Sin. 45:953-962.
International Search Report and Written Opinion in PCT/US2014/54917 dated Dec. 15, 2014.
International Preliminary Report on Patentability in PCT/US2014/54917 dated May 12, 2016.

* cited by examiner

SEQUENCE LISTING

```
<160> NUMBER OF SEQ ID NOS: 17

<210> SEQ ID NO 1
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 1
agcccagaaa aatttcatgg acacatacag                                      30
```

```
<210> SEQ ID NO 2
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 2
cccttgttct ggaggtgctc tcagatcttt                                      30

<210> SEQ ID NO 3
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 3
tttgctctat gcctgcttca                                                 20

<210> SEQ ID NO 4
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 4
ccatgaagag aaaggtccac a                                               21

<210> SEQ ID NO 5
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 5
atggtgaagg tcggtgtg                                                   18

<210> SEQ ID NO 6
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 6
cattctcggc cttgactg                                                   18

<210> SEQ ID NO 7
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 7
tatgccctcg ccatctgcct                                                 20

<210> SEQ ID NO 8
<211> LENGTH: 22
<212> TYPE: DNA
<213> ORGANISM: Artificial Sequence
<220> FEATURE:
<223> OTHER INFORMATION: Synthetic oligonucleotide
```

```
<400> SEQUENCE: 8
ccagcagtag gctctcatat gc                                             22

<210> SEQ ID NO 9
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 9
ggagctgaag ccactattta t                                              21

<210> SEQ ID NO 10
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 10
ctgtttgaag tggaccacat ca                                             22

<210> SEQ ID NO 11
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 11
cccggttcat tctgatactg ga                                             22

<210> SEQ ID NO 12
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 12
aactacccaa ggactcctac tgta                                           24

<210> SEQ ID NO 13
<211> LENGTH: 64
<212> TYPE: DNA
<213> ORGANISM: Artificial Sequence
<220> FEATURE:
<223> OTHER INFORMATION: Synthetic oligonucleotide

<400> SEQUENCE: 13
tgctgtccag tatcagaatg aaccgggttt tggccactga ctgacccggt tcactgatac     60
tgga                                                                 64

<210> SEQ ID NO 14
<211> LENGTH: 64
<212> TYPE: DNA
<213> ORGANISM: Artificial Sequence
<220> FEATURE:
<223> OTHER INFORMATION: Synthetic oligonucleotide

<400> SEQUENCE: 14
tgctgtacag taggagtcct tgggtagttt tggccactga ctgactaccc aagctcctac     60
tgta                                                                 64
```

```
<210> SEQ ID NO 15
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 15
caugaucuuc cagauuggag uucua                                         25

<210> SEQ ID NO 16
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 16
uagaacucca aucuggaaga ucaug                                         25

<210> SEQ ID NO 17
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 17
tactgcgcgt ggagacg                                                  17
```

METHOD FOR SELECTIVELY INHIBITING ACAT1 IN THE TREATMENT OF OBESITY, METABOLIC SYNDROME, AND ATHEROSCLEROSIS

This application is a U.S. National Stage Application of PCT/US2014/054917 filed Sep. 10, 2014 and claims the benefit of priority from U.S. Provisional Patent Application Ser. Nos. 61/897,318, filed Oct. 30, 2013, and 61/968,542, filed Mar. 21, 2014, the contents of each of which are incorporated herein by reference in their entireties.

INTRODUCTION

This invention was made with government support under grant numbers R01HL060306 and 1F32HL124953 awarded by the National Institutes of Health. The government has certain rights in the invention.

BACKGROUND

Obesity is a public health issue in the United States with more than one third of the adult population being identified as obese. Obesity in children is also on the rise. Obesity is also associated with an increased risk of a variety of co-morbid conditions such as diabetes, atherosclerosis and hypertension. Obesity also is one of the leading risk factors for metabolic syndrome. Metabolic syndrome is a group of five risk factors that increase an individual's risk for heart disease and other health problems such as diabetes and stroke. The five conditions or risk factors are high blood pressure, low HDL cholesterol levels in blood, large waistline, high triglyceride levels in blood, and high fasting blood sugar. Individuals with three or more of these conditions are diagnosed with metabolic syndrome. Metabolic syndrome is becoming an increasingly common diagnosis as the obesity rates rise in the United States, with health professionals predicting that, sometime in the near future, metabolic syndrome may overtake smoking as the leading risk factor for heart disease. It is known that one of the diseases that commonly develops in patients with metabolic syndrome is type II diabetes; in turn, the number one cause of death of patients with type II diabetes is atherosclerosis, a disease that causes plaques to build up in the arteries and eventually lead to heart attacks and stroke. As a result, there is a great deal of interest in identifying new targets for development of therapies to prevent and treat obesity, metabolic syndrome, and the conditions that can develop as a result, such as atherosclerosis.

Acyl-CoA:Cholesterol Acyltransferase (ACAT) converts free cholesterol to cholesterol ester, and is one of the key enzymes in cellular cholesterol metabolism. Two ACAT genes have been identified which encode two different enzymes, ACAT1 and ACAT2 (also known as SOAT1 and SOAT2). While both ACAT1 and ACAT2 are present in the liver and intestine, the cells containing either enzyme within these tissues are distinct, suggesting that ACAT1 and ACAT2 have separate functions. Both enzymes are potential drug targets for treating dyslipidemia and atherosclerosis.

WO 2003/088962 discloses combining administration of a PPARα/γ dual agonist compound with a compound that inhibits ACAT activity in order to treat lipid disorders as well as obesity. Nowhere does the application teach use of an ACAT inhibitor alone, or use of inhibitors specific for one ACAT isoform. Therefore, this application fails to teach that inhibiting ACAT1 specifically in macrophages would be beneficial in the treatment of obesity and/or atherosclerosis.

WO 2004/111084 discloses use of peptides that enhance cholesterol ester hydrolase activity (CEH) or inhibit ACAT activity to treat atherosclerosis. The application teaches use of peptides that target macrophage ACAT enzymes. WO 2006/0257466 also discloses combining CEH enhancers and ACAT inhibitors that are targeted to macrophages in the treatment of atherosclerosis. WO 2006/105666 teaches administering macrophage-targeted formulations that target modulation of ACAT activity alone for the treatment of atherosclerosis. The inhibitors mentioned were not isoform-specific, and no data were provided demonstrating that inhibition of ACAT1 specifically in macrophages would be beneficial for treatment of atherosclerosis or obesity.

U.S. Pat. No. 6,121,283 discloses treatments for obesity that involve administration of ApoB/MTP inhibitors as the primary agents, and then potentially combining these agents with inhibitors of a variety of targets including ACAT.

WO 2009/081957 discloses use of a drug, beauveriolide, to inhibit activity of ACAT2, but not ACAT1, as a treatment for lipid disorders as well as obesity. KR 1020030011474 discloses use of a drug, panaxynone A, a polyacetylene compound, to suppress activity of ACAT. Also taught is the use of this drug to suppress obesity by reducing body weight.

U.S. Patent Application No. 2011/0184173 and EP 2228376 disclose administration of pyripyropene derivatives for inhibiting activity of ACAT2, but not ACAT1. Also taught is the use of these compounds to treat a variety of conditions including disorders of lipid metabolism and obesity.

Stahlberg et al. (1997. *Hepatology* 25:1447-1450) studied hepatic cholesterol metabolism in obese and non-obese subjects. They reported increases in ACAT activity in obese subjects and attributed these increased levels of ACAT activity to higher concentrations of microsomal free cholesterol. Obese subjects also exhibited large increases in cholesteryl esters in liver. Nowhere does this paper teach or suggest that obesity could be treated or prevented by administration of ACAT inhibitors.

Turkish and Sturley (2007. *Am J. Physiol. Gastrointest. Liver Physiol.* 292:G953-G957) discuss the role of neutral lipid metabolism in the pathogenesis and/or treatment of diseases including obesity. As discussed in this review paper, the apparent redundancy in neutral lipid synthesis is advantageous, and marked changes in lipid homeostasis arise when expression of acyl CoA:diacylglycerol acyltransferase (DGAT), in particular, is altered. The authors speculate that isoform-specific inhibition of DGAT1, DGAT2, ACAT2 or the acyl-CoA wax alcohol acyltransfereases (AWATs) may be effective and non-toxic therapeutics for type II diabetes and obesity, for example. No specific data are provided showing any effect of ACAT1 or ACAT2 inhibition to prevent or treat obesity. This paper also failed to disclose any role for modulating macrophage-specific ACAT1 activity as a method of treating obesity and/or atherosclerosis.

Tomoda and Omura (2007. *Pharmacol. & Therapeut.* 115:375-389) discussed potential therapeutics for obesity and atherosclerosis. The class of compounds disclosed was neutral lipid metabolism inhibitors isolated from microorganisms. Both DGAT and ACAT inhibitors were discussed, including both synthetic compounds and compounds of microbial origin. The synthetic ACAT inhibitors included pactimibe, avasimibe, Wu-V-23 and CL-283,546. The microbial origin compounds included pyripyropene, pyripyropene derivatives A through D, purpactin A, purpactin B, purpactin C, glisoprenin A, glisoprenin B, terpendole C, terpendole D, beauvericin, spylidone, and sespendole. As discussed, the authors indicated that the selectivity of ACAT inhibitors toward ACAT1 and ACAT2 is only partially understood. The authors concluded that DGAT and ACAT have been identified as potential therapeutic targets. DGAT1 knockout mice are reported to be resistant to obesity, while DGAT2 knockout mice die soon after birth, making DGAT1 a more promising target for anti-obesity therapeutics. The only actual data discussed with respect to ACAT inhibition, however, related to the activity of ACAT inhibitors in the treatment of atherosclerosis, not obesity itself.

The role of ACAT proteins in promoting or protecting against atherosclerosis, co-morbidity associated with obesity, has been investigated. Rudel et al. (2005. *Arterioscler. Thromb. Vasc. Biol.* 25:1112-1118) proposed that decreased activity, i.e., inhibition, of ACAT2 is atheroprotective. These authors also predicted that the role of ACAT1 activity is to destabilize cellular membrane function and promote macrophage cell death. The prediction made by these authors (i.e., decreased ACAT1 activity in macrophages can lead to macrophage cell death in vivo) was based on in vitro data only. The authors suggested that ACAT2 is more important as a target for treating coronary artery disease, but provide no in vivo data on the role of ACAT1. In a review article, Lopez-Farre et al. (2008. *Cardiovasc. Ther.* 26:65-74) proposed a new anti-atherosclerosis drug (eflucimibe) for use clinically; the drug is a non-selective ACAT inhibitor. Daugherty et al. (2008. *Circ. Res.* 102:1445-1447) discussed macrophage accumulation at the site of atherosclerotic lesions and proposed this accumulation as a factor in growth of atherosclerotic lesions, but stated that the role for ACAT1 in macrophages had not yet been elucidated.

Hongo et al. (2009. *Am. J. Physiol. Endocrinol. Metab.* 297:E474-E482) focused on a link between ACAT1 gene expression in macrophages and leptin activity. The authors reported that leptin accelerates accumulation of cholesteryl ester in macrophages that is mediated by increased ACAT1 expression.

Yoshinaka et al. (2010. *Atherosclerosis* 213:85-91) performed in vivo studies in mice and reported that an ACAT1-specific inhibitor (K604) stimulated procollagen production independent of ACAT1 activity in macrophages, where the lesions exhibited an increase in collagen-positive areas and a decrease in macrophage-positive areas. The authors suggested that this would be a favorable plaque phenotype, indicating they provided the first evidence that an ACAT1-selective inhibitor had effects on smooth muscle cells independent of macrophage ACAT1 activity. These authors suggested that inhibiting ACAT1 might be beneficial to atherosclerosis; however, they did not demonstrate that inhibiting ACAT1, either by global inhibition or by inhibiting ACAT1 specifically in macrophages, might reduce atherosclerotic lesion, nor did they demonstrate that an ACAT1-specific inhibitor might provide benefits in obesity.

Xu et al. (2013. *Acta. Biochim. Biophys. Sin.* 45:953-962) disclosed that microRNAs targeted to ACAT1, and tested in vitro, reduced human ACAT1 expression and resulted in decreased macrophage foam cell formation. Another paper from the same laboratory (Huang et al. 2013. *Arterioscler. Thromb. Vasc. Biol.* 33:2081-2087) investigated the effect of ACAT1 inhibition as a method for treating leukemia. ACAT1 knockout mice were used. Although the focus of the paper was treatment of leukemia, and no experiments were performed in an animal model of atherosclerosis, the authors suggested that both ACAT1 and ACAT2 are targets for treating atherosclerosis. The authors proposed that partial inhibition of ACAT1 may be beneficial in atherosclerosis since total knockout of ACAT1 in mice resulted in worsening of the disease.

Various ACAT inhibitors have been shown to be effective to reduce atherosclerosis in different animal models, for either early stage or advanced stage of atherosclerosis (Rong et al. 2013. *Arterioscler. Thromb. Vasc. Biol.* 33:4-12; Rival et al. 2002. *J. Cardiovasc. Pharmacol.* 39(2):181-91; Bocan et al. 2000. *Arterioscler. Thromb. Vasc. Biol.* 20(1):70-9; López-Fárre et al. 2008. *Cardiovasc. Ther.* 26:65-74; Kusunoki et al. 2001. *Circulation* 103(21):2604-9), suggesting that ACAT inhibition can be a potential strategy for treating hypercholesterolemia and atherosclerosis. In these studies, however, the ACAT inhibitors administered to laboratory animals were not targeted at specific tissues. Additionally, it must be remembered that ACAT enzymes are members of the membrane-bound O-acyltransferase (MBOAT) enzyme family. MBOATs are multi-span membrane enzymes that utilize fatty acyl-CoA and a hydrophobic substance as their substrates. In humans, there are 11 MBOAT enzymes with distinct functions (Chang & Chang. 2011. *Front. Biol.* 6:177-182). The ACAT inhibitors used in experiments described above may produce off target effects by inhibiting other members in the MBOAT enzyme family as well.

SUMMARY OF THE INVENTION

The present invention features methods for preventing and treating diet-induced obesity, metabolic syndrome, and atherosclerosis. It has been found that selective inhibition of ACAT1 in myeloid cells induces resistance to high fat diet-induced obesity in vivo. In addition to inducing resistance to diet-induced obesity, the other effects observed in vivo included increased insulin sensitivity (decreased insulin resistance), decreased number of infiltrating macrophages in adipose tissue, and smaller fat cell size.

It has also been found that targeted inhibition of ACAT1 in monocytes/macrophages retarded progression of atherosclerosis, and attenuated metabolic syndrome, in an in vivo mouse model. ACAT1 inhibitors of use in preventing or treating obesity, metabolic syndrome, and atherosclerosis particularly include compounds selective for ACAT1 inhibition or for ACAT1 protein depletion. Examples of such agents are those with $IC_{50}$ values for ACAT1 which are at least twice the corresponding $IC_{50}$ value for ACAT2. In a preferred embodiment, the inhibitor inhibits the enzyme activity, or the expression of ACAT1 protein in macrophages. In yet another embodiment, the ACAT1 inhibitor is a siRNA against ACAT1 formulated in an exosome, liposome, or nanoparticle, that is targeted to monocytes/macrophages.

DETAILED DESCRIPTION OF THE INVENTION

ACAT1 is an enzyme that catalyzes the conversion of cellular cholesterol to cholesteryl esters for storage. It has now been found that inhibition of ACAT1 in myeloid cells, e.g., monocytes and macrophages, induces resistance to high fat diet-induced obesity in vivo using a myeloid-specific Acat1 knockout mouse strain ($Acat1^{-M/-M}$). In addition to inducing resistance to diet-induced obesity, the other effects observed in vivo included increased insulin sensitivity (decreased insulin resistance) and fewer infiltrating macrophages in adipose tissue, as well as smaller fat cell size.

In addition, using the macrophage-specific Acat1 knockout mouse model (i.e., $Acat1^{-M/-M}$) it has now been shown that the macrophage-specific Acat1 phenotype is associated with reductions atherosclerotic risks, as well as lower steady state blood glucose and steady state blood insulin levels. These results demonstrated that inhibition of ACAT1 specifically in macrophages would be useful in the treatment of atherosclerosis and metabolic syndrome.

When considered together with other aspects of the present invention, inhibition of ACAT1 specifically in macrophages is of particular use in preventing and treating obesity, a risk factor for both atherosclerosis and metabolic syndrome. In this respect, ACAT1 inhibition in macrophages is also of use in preventing and/or treating metabolic syndrome, specifically the co-morbidity of coronary artery disease (atherosclerosis).

Accordingly, the present invention features methods for preventing and treating three related diseases alone or in combination: diet-induced obesity, metabolic syndrome, and atherosclerosis. The present invention is also a method for increasing insulin resistance, for reducing fat cell size, slowing migration of macrophages to sites of inflammation in adipose tissue, and for reducing or preventing atherosclerotic lesion development in vascular tissue. In accordance with the methods of this invention, a subject having or predisposed to diet-induced obesity, alone or in combination with atherosclerosis, would be administered an effective amount of an agent that selectively inhibits the activity of ACAT1 in myeloid cells (i.e., an ACAT1-selective inhibitor targeted at myeloid cells, including monocytes and macrophages) so that diet-induced obesity and its resulting conditions (i.e., metabolic syndrome and/or atherosclerosis) is prevented or treated, wherein successful treatment would be associated with a reduction in fat tissue content and body weight in an individual, and also a reduction in risk of developing metabolic syndrome and atherosclerosis. Reduced risk of these conditions could be monitored by tracking the beneficial effects shown to be produced by the macrophage-specific Acat1 inhibition that would include but not be limited to lower blood glucose and insulin levels, increased insulin sensitivity, decreased macrophage accumulation at sites of atherosclerotic plaque formation, and decreased plaque size.

As used herein, a "selective inhibitor of ACAT1" or "ACAT1-selective inhibitor" is any molecular species that is an inhibitor of the ACAT1 enzyme in myeloid cells, but which fails to inhibit, or inhibits to a substantially lesser degree ACAT2. Methods for assessing the selectively of ACAT1 inhibitors are known in the art and can be based upon any conventional assay including, but not limited to the determination of the half maximal (50%) inhibitory concentration (IC) of a substance (i.e., 50% IC, or $IC_{50}$), the binding affinity of the inhibitor (i.e., $K_i$), and/or the half maximal effective concentration ($EC_{50}$) of the inhibitor for ACAT1 as compared to ACAT2. See, e.g., Lada et al. 2004. *J. Lipid Res.* 45:378-386 and U.S. Pat. No. 5,968,749. ACAT1 and ACAT2 proteins that can be employed in such assays are well-known in the art and set forth, e.g., in GENBANK Accession Nos. NP_000010 (human ACAT1) and NP_005882 (human ACAT2). See also U.S. Pat. No. 5,834,283.

In particular embodiments, ACAT1-selective inhibitors are agents that exhibit an $IC_{50}$ value for ACAT1 that is at least twice or, more desirably, at least three, four, five, or six times lower than the corresponding $IC_{50}$ value for ACAT2. Most desirably, an ACAT1-selective inhibitor has an $IC_{50}$ value for ACAT1 which is at least one order of magnitude or at least two orders of magnitude lower than the $IC_{50}$ value or ACAT2.

Selective inhibitors of ACAT1 activity have been described. See, e.g., inhibitors listed in Table 1. For example, Ikenoya et al. (2007. *Atherosclerosis* 191:290-297) teach that K-604 has an $IC_{50}$ value of 0.45 µmol/L for human ACAT1 and 102.85 µmol/L for human ACAT2. As such K-604 is 229-fold more selective for ACAT1 than ACAT2. In addition, diethyl pyrocarbonate has been shown to inhibit ACAT1 with 4-fold greater activity ($IC_{50}$=44 µM) compared to ACAT-2 ($IC_{50}$=170 µM) (Cho et al. 2003. *Biochem. Biophys. Res. Comm.* 309:864-872). Ohshiro et al. (2007. *J. Antibiotics* 60:43-51) teach selective inhibition with beauveriolides I (0.6 µM vs. 20 µM) and III (0.9 µM vs. >20 µM) for ACAT1 over ACAT2. In addition, beauveriolide analogues 258, 280, 274, 285, and 301 show ACAT1-selective inhibition with $pIC_{50}$ values in the range of 6 to 7 (Tomoda & Doi. 2008. Accounts Chem. Res. 41:32-39). Lada et al. (2004. *J. Lipid Res.* 45:378-386) teach a Warner-Lambert compound (designated therein as Compound 1A), and derivatives thereof (designated Compounds 1B, 1C, and 1D), which inhibit ACAT1 more efficiently than ACAT2 with $IC_{50}$ values 66- to 187-fold lower for ACAT1 than for ACAT2 (see Table 1). Moreover, Lee et al. (2004. *Bioorg. Med. Chem. Lett.* 14:3109-3112) teach methanol extracts of *Saururus chinensis* root that contain saucerneol B and manassantin B for inhibiting ACAT activity. Saucerneol B inhibited hACAT-1 and hACAT-2 with $IC_{50}$ values of 43.0 and 124.0 µM, respectively, whereas manassantin B inhibited hACAT-1 and hACAT-2 with $IC_{50}$ values of 82.0 µM and only 32% inhibition at 1 mM, respectively.

TABLE 1

| Inhibitor | Structure | $IC_{50}$ ACAT1 | ACAT2 |
|---|---|---|---|
| K-604 | 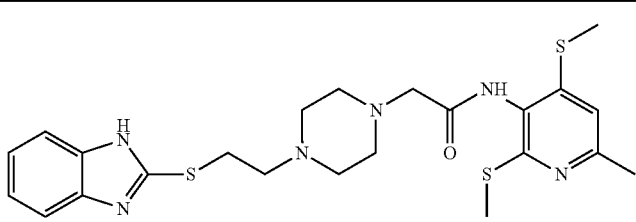 2-[4-[2-(benzimidazol-2-ylthio)ethyl]piperazin-1yl]-N-[2,4-bis(methylthio)-6-methyl-3-pyridyl]acetamide | 0.45 µmol/L | 102.85 µmol/L |

TABLE 1-continued

| Inhibitor | Structure | IC$_{50}$ ACAT1 | IC$_{50}$ ACAT2 |
|---|---|---|---|
| Beauveriolide I | 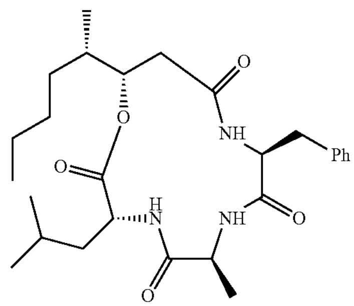 [SMILES: CCCC[C@H](C)[C@@H]1CC(=O)N[C@@H](Cc2ccccc2)C(=O)N[C@@H](C)C(=O)N[C@H](CC(C)C)C(=O)O1] | 0.6 μM | 20 μM |
| Beauveriolide III | 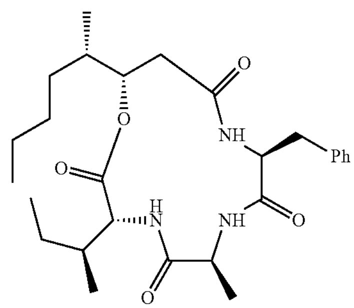 [SMILES: CCCC[C@H](C)[C@@H]1CC(=O)N[C@@H](Cc2ccccc2)C(=O)N[C@@H](C)C(=O)N[C@H]([C@@H](C)CC)C(=O)O1] | 0.9 μM | >20 μM |
| Eflucimibe (F12511) | 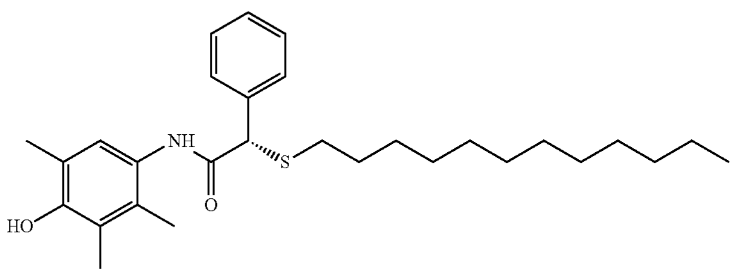 [SMILES: CCCCCCCCCCCCS[C@H](C(=O)Nc1cc(C)c(O)c(C)c1C)c1ccccc1] | 39 nM | 110 nM |
| Compound 1A | 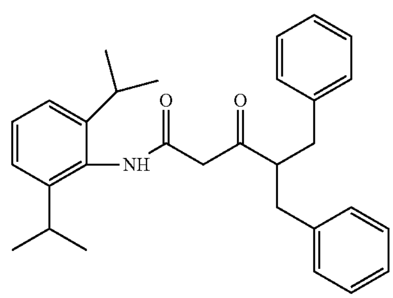 [SMILES: CC(C)c1cccc(C(C)C)c1NC(=O)CC(=O)C(Cc1ccccc1)Cc1ccccc1] | 4.2 nM | 275 nM |
| Compound 1B | 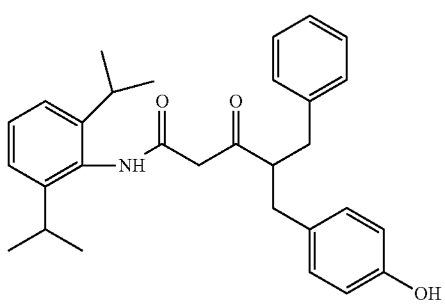 [SMILES: CC(C)c1cccc(C(C)C)c1NC(=O)CC(=O)C(Cc1ccccc1)Cc1ccc(O)cc1] | 10.3 nM | 1500 nM |

TABLE 1-continued
| Inhibitor | Structure | IC$_{50}$ ACAT1 | IC$_{50}$ ACAT2 |
|---|---|---|---|
| Compound 1C | 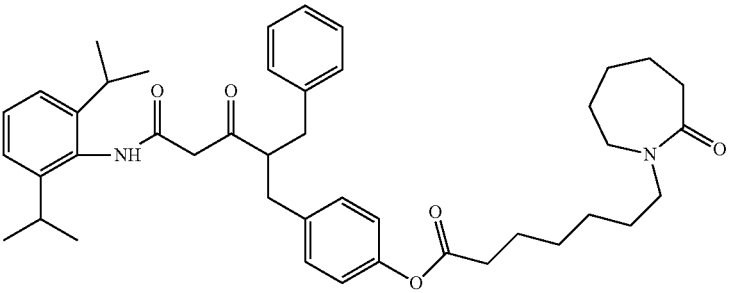 [SMILES: CC(C)c1cccc(C(C)C)c1NC(=O)CC(=O)C(Cc1ccccc1)Cc1ccc(OC(=O)CCCCCCN2CCCCCC2=O)cc1] | 3.6 nM | 530 nM |
| Compound 1D | 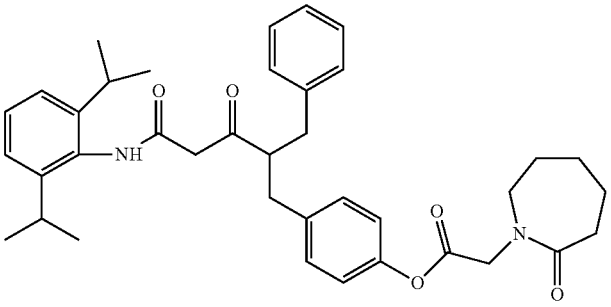 [SMILES: CC(C)c1cccc(C(C)C)c1NC(=O)CC(=O)C(Cc1ccccc1)Cc1ccc(OC(=O)CN2CCCCCC2=O)cc1] | 3.2 nM | 600 nM |
| 1[a] | 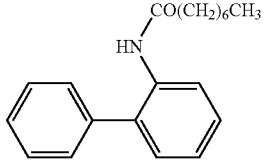 | 61 μM | 230 μM |
| 2[a] | 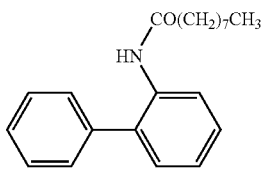 | 65 μM | 414 μM |
| 13[a] | 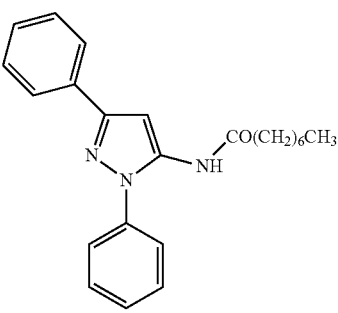 | 24 μM | 53 μM |

TABLE 1-continued

| Inhibitor | Structure | IC$_{50}$ ACAT1 | IC$_{50}$ ACAT2 |
|---|---|---|---|
| 14[a] | 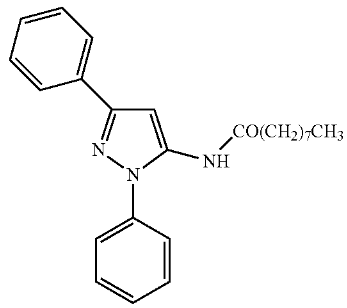 | 23 μM | 75 μM |
| 16[a] | 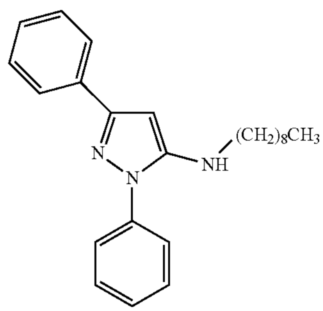 | 39 μM | 97 μM |

[a]Gelain (June 2006) 10th ISCPP, Strasbourg, France.

Desirably, ACAT1-selective inhibitors of the present invention have an IC$_{50}$ value in the range of 1 nM to 100 μM. More desirably, ACAT1-selective inhibitors of the invention have an IC$_{50}$ value less than 100 μM, 50 μM, 10 μM, or 1 μM. Most desirably, ACAT1-selective inhibitors of the invention have an IC$_{50}$ value in the nM range (e.g., 1 to 999 nM).

In addition to the above-referenced ACAT1-selective inhibitors, it is contemplated that any conventional drug screening assay can be employed for identifying or selecting additional or more selective ACAT1 inhibitors or derivatives or analogs of known ACAT1 inhibitors. See, e.g., Lada et al. (2004) *J. Lipid Res.* 45:378-386. Inhibitors of use in the invention can be derivatives of known ACAT inhibitors, which are selective for ACAT1 or can be identified and obtained from libraries of compounds containing pure agents or collections of agent mixtures.

Known ACAT inhibitors include derivatives of anilidic, ureidic or diphenyl imidazole compounds.

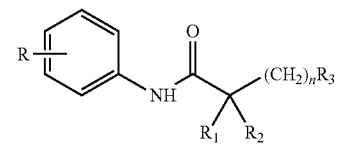

Anilidic
Inhibitors

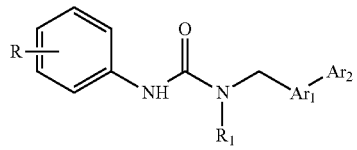

Ureidic
Inhibitors

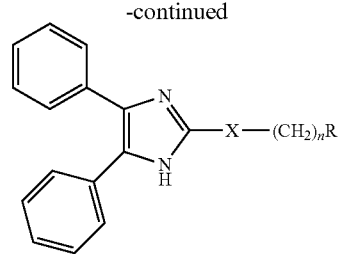

Diphenyl Imidazole
Inhibitors

Examples of pure agents for library screens include, but are not limited to, proteins, peptides, nucleic acids, oligonucleotides, carbohydrates, lipids, synthetic or semi-synthetic chemicals, and purified natural products. Examples of agent mixtures include, but are not limited to, extracts of prokaryotic or eukaryotic cells and tissues, as well as fermentation broths and cell or tissue culture supernatants. In the case of agent mixtures, one may not only identify those crude mixtures that possess the desired activity, but also monitor purification of the active component from the mixture for characterization and development as a therapeutic drug. In particular, the mixture so identified may be sequentially fractionated by methods commonly known to those skilled in the art which may include, but are not limited to, precipitation, centrifugation, filtration, ultrafiltration, selective digestion, extraction, chromatography, electrophoresis or complex formation. Each resulting subfraction may be assayed for the desired activity using the original assay until a pure, biologically active agent is obtained.

Library screening can be performed in any format that allows rapid preparation and processing of multiple reactions such as in, for example, multi-well plates of the 96-well variety. Stock solutions of the agents as well as assay components are prepared manually and all subsequent pipetting, diluting, mixing, washing, incubating, sample readout and data collecting is done using commercially available robotic pipetting equipment, automated work stations, and analytical instruments for detecting the signal generated by the assay. Examples of such detectors include, but are not limited to, luminometers, spectrophotometers, calorimeters, and fluorimeters, and devices that measure the decay of radioisotopes. It is contemplated that any suitable ACAT enzymatic assay can be used in such screening assays. Moreover, preclinical efficacy of ACAT1 inhibitors can be assessed using conventional animal models of obesity. Examples of models that are available would include, but not be limited to, a cat model for human obesity and diabetes (Hoenig. 2012. *J. Diabetes Sci. Technol.* 6:525-533), rat models for obesity (e.g., Song et al. 2013. *PLoS ONE* 8(7):e69925; Cabiati et al. 2013. *PLoS ONE* 8(8): e72959; Fellmann et al. 2013. *Pharmacol. Ther.* 137:331-340), mouse models for obesity (e.g., Respondek et al. 2013. *PLoS ONE* 8(8):e71026; Fellmann et al. 2013. *Pharmacol. Ther.* 137:331-340; Aprahamian. 2013. *Metabolism* 62(12): 1730-8), a gerbil model for diabetes and obesity (Bouderba et al. 2013. *J. Diabetes* 6(2):184-92), and a pig model of metabolic syndrome (te Pas et al. 2013. *PLoS ONE* 8(9): e73087). One of skill it the art would choose an appropriate model for use in screening ACAT1 inhibitors.

As disclosed herein, there are a number of suitable molecules that selectively inhibit the activity of ACAT1 without modulating the expression of ACAT1. Accordingly, in one embodiment of the present invention, a "selective inhibitor of ACAT1" or "ACAT1-selective inhibitor" specifically includes molecules such as small inhibitory RNA (siRNA), antisense molecules, or ribozymes. However, in alternative embodiments, the ACAT1 selective inhibitor is a molecule, which selectively inhibits the expression of ACAT1, without modulating the expression of ACAT2. As is conventional in the art, siRNA or microRNA refer to noncoding RNAs from 19-25 nucleotides in length derived from endogenous genes that act as post-transcriptional regulators of gene expression. They are processed from longer (ca 70-80 nucleotide) hairpin-like precursors termed pre-miR-NAs by the RNAse III enzyme Dicer. MicroRNAs assemble in ribonucleoprotein complexes termed miRNPs and recognize their target sites by antisense complementarity thereby mediating down-regulation of their target genes. By way of illustration, target sequences for siRNA or artificial micro-RNA molecules against mouse ACAT1 gene include, but are not limited to, those listed in Table 3 as SEQ ID NOs:9-12. SiRNA or artificial microRNAs against human ACAT1 gene (e.g., GENBANK Accession No. NM_000019, incorporated by reference) were also generated and shown to decrease human ACAT1 protein expression by 80% in human cells. Exemplary microRNA sequences targeting human ACAT1 include, but are not limited, those listed in Table 5. In a similar manner, artificial microRNA against the ACAT1 gene in primates (e.g., GENBANK Accession No. XM_508738, incorporated by reference) can be developed, and used to selectively inhibit the expression of primate ACAT1.

Artificial microRNA or siRNA molecules which selectively inhibit the expression of ACAT1 can be administered as naked molecules, delivered via liposomes or exosomes, or via vectors (e.g., a plasmid or viral vector such as an adenoviral, lentiviral, retroviral, adeno-associated viral vector or the like) harboring nucleic acids encoding the microRNA. Desirably, a vector used in accordance with the invention provides all the necessary control sequences to facilitate expression of the microRNA. Such expression control sequences can include but are not limited to promoter sequences, enhancer sequences, etc. Such expression control sequences, vectors and the like are well-known and routinely employed by those skilled in the art.

As indicated, selective inhibitors of ACAT1 find application in methods for inducing resistance to diet-induced obesity, increasing insulin sensitivity, decreasing the number of infiltrating macrophages in adipose tissue, decreasing fat cell size, lowering steady state blood glucose levels and insulin levels, decreasing insulin resistance, decreasing the number of infiltrating macrophages in activated aortic endothelium, and reducing atherosclerotic lesion formation in blood vessels. Generally, such methods involve administering to a subject in need of treatment an ACAT1-selective inhibitor in an amount that effectively reduces the activity of ACAT1 by at least 60%, 70%, 80%, 90%, 95%, 99% or 100%. Subjects benefiting from treatment with an agent of the invention include obese subjects with or without peripheral insulin resistance (type II diabetes), or subjects predisposed to obesity (e.g., subjects with a family history of obesity and/or type II diabetes). Subjects benefiting from treatment with an agent of the invention include those with metabolic syndrome or those with active atherosclerotic processes or at risk of developing atherosclerosis. In the context of this invention, a subject can be any mammal including human, companion animals (e.g., dogs or cats), livestock (e.g., cows, sheep, pigs, or horses), or zoological animals (e.g., monkeys). In particular embodiments, the subject is a human.

While certain embodiments of this invention embrace in vivo applications, in vitro use of agents of the invention are also contemplated for examining the effects of ACAT1 inhibition on myeloid cell expression of Acat1 or activity of ACAT1. In addition to treatment, agents of the invention also find application in monitoring the phenotypic consequences (e.g., expression or activity of leptin and other adipocytokines, fat cell size, level of insulin resistance, level of macrophages in adipose tissue or in atherosclerotic plaque, atherosclerotic lesion development, increased level of steady state blood glucose and insulin, etc.) of obesity and/or metabolic syndrome.

When used in therapeutic applications, an ACAT1-selective inhibitor of the invention will have the therapeutic benefit of inducing resistance to diet-induced obesity, increasing peripheral insulin sensitivity, lowering circulating levels of leptin and adipocytokines, decreasing the number of infiltrating macrophages in adipose tissue, decreasing fat cell size in the subject, decreasing steady state glucose and/or insulin levels, and decreasing atherosclerotic lesion development as compared to subjects not receiving treatment with the ACAT1-selective inhibitor. Successful clinical use of an ACAT1-selective inhibitor can be determined by the skilled clinician or veterinarian based upon routine clinical practice.

For therapeutic use, ACAT1-selective inhibitors can be formulated with a pharmaceutically acceptable carrier at an appropriate dose. Such pharmaceutical compositions can be prepared by methods and contain carriers which are well-known in the art. A generally recognized compendium of such methods and ingredients is Remington: The Science and Practice of Pharmacy, Alfonso R. Gennaro, editor, 20th ed. Lippincott Williams & Wilkins: Philadelphia, Pa., 2000. A pharmaceutically acceptable carrier, composition or vehicle, such as a liquid or solid filler, diluent, excipient, or solvent encapsulating material, is involved in carrying or transporting the subject agent from one organ, or portion of the body, to another organ, or portion of the body. Each carrier must be acceptable in the sense of being compatible with the other ingredients of the formulation and not injurious to the patient.

Examples of materials which can serve as pharmaceutically acceptable carriers include sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; pH buffered solutions; polyesters, polycarbonates and/or polyanhydrides; and other non-toxic compatible substances employed in pharmaceutical formulations. Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Compositions of the present invention can be administered parenterally (for example, by intravenous, intraperitoneal, subcutaneous or intramuscular injection), topically, orally, intranasally, intravaginally, or rectally according to standard medical practices.

In preferred embodiments of the present invention, the ACAT1-selective inhibitor is selectively delivered to myeloid cells, in particular macrophages. It has been established that adipose tissue macrophages are involved in the physiological responses to diet-induced obesity (e.g., Weisberg et al. 2003. *J. Clin. Invest.* 112:1796-1808; Lumeng et al. 2007. *Diabetes* 56:16-23). For the purposes of the present invention, "selective delivery to myeloid cells" or "selectively delivered to myeloid cells" is intended to mean that the agent is administered directly to, or targeted to, the myeloid cells of the subject. It has been shown that targeted liposomes, or targeted nanoparticles, or targeted exosomes (i.e., natural transport nanovesicles in the range of 40-100 nm and bears ligands that are recognized by macrophages), are a useful technology for cell-targeted delivery of agents that inhibit protein activity in cells. Accordingly, in one embodiment of the present invention, the ACAT1-selective inhibitor is delivered to the myeloid cells via a targeted liposome, or targeted nanoparticles, or a targeted exosome. Exosomes of use in this invention can be prepared by conventional methods, see, e.g., Sun et al. 2010. *Mol. Ther.* 18:1606-1614. In particular embodiments, the exosome is modified with a moiety that targets myeloid cells. For example, adipose tissue macrophages, or ATMs, are known to have specific cell markers that can be used as targeting moieties for preparing exosomes that target ATMs. Such ATM cell markers have been described in the literature and include, but are not limited to, F4/80$^+$ (Weisberg et al. 2003. *J. Clin. Invest.* 112:1796-1808), CD11b and CD11c (Lumeng et al. 2007. *J. Clin. Invest.* 121:2111-17; Nguyen et al. (2007) *J. Biol. Chem.* 282:35279-92), genes important in macrophage-induced lipid metabolism such as Pparg, Adfp, Srepf1, and Apob48r (Lumeng et al. 2007. *Diabetes* 56:16-23), and neuropeptide Y (Singer et al. 2013. *PLoS ONE* 8(3):e57929). One or more ACAT1-selective inhibitors can be encapsulated within liposomes or nanoparticles, or exosomes by conventional methods, e.g., incubating the therapeutic agent with targeted liposomes, targeted nanoparticles, or targeted exosomes, prepared in saline at room temperature for several minutes, and separating the liposomes, nanoparticles or exosomes from un-encapsulated drug and debris, e.g., by sucrose gradient separation.

The selected dosage level of an ACAT1-selective inhibitor will depend upon a variety of factors including the activity of the particular agent of the present invention employed, the route of administration, the time of administration, the rate of excretion or metabolism of the particular agent being employed, the duration of the treatment, other drugs, compounds and/or materials used in combination with the particular agent employed, the age, sex, weight, condition, general health and prior medical history of the patient being treated, and other factors well-known in the medical arts.

A physician or veterinarian having ordinary skill in the art can readily determine and prescribe the effective amount of the pharmaceutical composition required based upon the administration of similar compounds or experimental determination. For example, the physician or veterinarian could start doses of an agent at levels lower than that required in order to achieve the desired therapeutic effect and gradually increase the dosage until the desired effect is achieved. This is considered to be within the skill of the artisan and one can review the existing literature on a specific agent or similar agents to determine optimal dosing.

The invention is described in greater detail by the following non-limiting examples.

Example 1: Materials and Methods

Mice.

Mice were fed ad libitum with standard chow diet, maintained in a pathogen-free environment in single-ventilated cages and kept on a 12 hour light/dark schedule.

Generation of Acat1$^{-M/-M}$ and Acat1$^{-/-}$ and Acat2$^{-/-}$ Mice.

Methods for generation of Acat1 knockout mice are known in the art (Meiner et al. 1996. *Proc. Natl. Acad. Sci. USA* 93:14041-14; Buhman et al. 2000. *Nat. Med.* 6:1341-1347). Myeloid-specific knockout of ACAT1 (Acat1$^{-M/-M}$ mice) was achieved with the Cre-lox system in accordance with conventional methods. See, e.g., Cole et al. 2012. *Mediat. Inflamm.* 2012:851798; Zhu et al. 2008 *J. Biol. Chem.* 283:22930-41. Generally, mice with macrophage-specific deletion of Acat1 were generated by crossing Acat1 floxed (Acat1$^{flox/flox}$) mice with C57BL/6 mice expressing the Cre recombinase transgene under control of the lysozyme M promoter (B6.129-Lyzs$^{tm1(cre)Ifo}$/J, The Jackson Laboratory). Progeny from the cross that were heterozygous at the Acat1 locus and inherited the LysCre allele were identified by PCR (i.e., Acat1$^{+-M}$). Intercrossing Acat1$^{+/-M}$ mice resulted in the production of the Acat1$^{+/+}$ (WT), Acat1$^{+/-M}$ (heterozygous), and Acat1$^{-M/-M}$ (homozygous) mice.

ACAT Activity Assay, Immunoprecipitation (IP) and Immunoblot Analyses.

Freshly isolated samples were homogenized on ice in 50 mM Tris, 1 mM EDTA, pH 7.8 and solubilized in detergent using 2.5% CHAPS and 1 M KCl. The homogenates were centrifuged at 100,000 g for 45 minutes. The supernatants were used for ACAT activity assay in mixed micelles, and for IP and immunoblot analyses (Chang et al. 1998. *J. Biol. Chem.* 273:35132-35141; Chang et al. 2000. *J. Biol. Chem.* 275:28083-28092).

RNA Isolation, RT-PCR, and Real-Time PCR. Total RNA was isolated with TRIZOL reagent (Invitrogen), stored at −80° C., and used for RT-PCR experiments, using the protocol supplied by the manufacturer. Real-time PCR was performed using the DYNAMO HS SYBR Green qPCR kit (New England Biolabs). Relative quantification was determined by using the delta delta CT method (Pfaffl et al. 2002. *Nucleic Acids Res.* 30:e36). Mouse ACAT1 primers were designed using Oligo 4.0 Primer Analysis Software. Mouse ACAT2, neurofilament 120-kD (NF120), GAPDH primers sequences are known in the art (Sakashita et al. 2003. *Lab. Invest.* 83:1569-1581; Kuwahara et al. 2000. *Biochem. Biophys. Res. Commun.* 268:763-766; Pan et al. 2007. *BMC Mol. Biol.* 8:22). Sequences of primers used herein are listed in Table 2.

TABLE 2

| Gene | Amplicon Size | Sense/Antisense (5'->3') | SEQ ID NO: |
|---|---|---|---|
| ACAT1 | 274 | AGCCCAGAAAAATTTCATGGACACATACAG | 1 |
|  |  | CCCTTGTTCTGGAGGTGCTCTCAGATCTTT | 2 |
| ACAT2 | 530 | TTTGCTCTATGCCTGCTTCA | 3 |
|  |  | CCATGAAGAGAAAGGTCCACA | 4 |
| GAPDH | 186 | ATGGTGAAGGTCGGTGTG | 5 |
|  |  | CATTCTCGGCCTTGACTG | 6 |

The PCR reaction conditions for amplification of ACAT1, ACAT2 and GAPDH included an initial denaturation at 94° C. for 5 minutes. Subsequently, 40 cycles of amplification were performed which included: denaturation at 94° C. for 10 seconds, annealing at 56° C. for 20 seconds, and elongation at 72° C. for 29 seconds. Amplification conditions for the remaining primers listed in Table 2 were as previously described (Van Eck et al. 2003. *J. Biol. Chem.* 278:23699-23705).

In Situ Hybridization, Immunohistochemical and Thioflavin S Staining.

In situ hybridization was performed using standard procedures (Poirier et al. 2008. *J. Biol. Chem.* 283:2363-2372) Immunohistochemistry was performed according to standard methods (Oddo et al. (2003) supra). Thioflavin S staining was according to the protocol as described (Guntern et al. 1992. *Experientia* 48:8-10), using free-floating sections. Confocal analysis of thioflavin S-positive amyloid deposits was performed using known methods (Dickson & Vickers 2001. *Neuroscience* 105:99-107).

Mouse Model for Macrophage-Specific Acat1$^{-/-}$ (Acat1$^{loxP}$). To create the Acat1 mouse line, the Acat1$^{-/-}$ (Acat1$^{loxP}$). To create the Acat1$^{loxP}$ mouse line, the Acat1$^{loxP}$ construct was transfected into mouse ES cells of C57/B6 origin to undergo homologous recombination and produce the Acat1$^{loxP}$ transgenic mice. The PCR primers employed to genotype the Acat1loxP transgenic mice were: SDL2: 5'-TAT GCC CTC GCC ATC TGC CT-3' (SEQ ID NO:7); LOX1: 5'-CCA GCA GTA GGC TCT CAT ATG C-3' (SEQ ID NO:8). Apoe$^{-/-}$/Acat1$^{-M/-M}$ mice (DKO mice) were generated by crossing Acat1$^{-M/-M}$ mice with Apoe$^{-/-}$ mice. Mice were housed in a specific pathogen-free barrier facility and fed with standard chow diet. For atherosclerosis studies, mice at 8-week-old were fed with Modified Paigen's diet (without cholate) for 12 weeks. Animal care and procedures were performed in accordance with the guidelines of the Animal Care and Use Committee at Dartmouth College.

Isolation of Peritoneal Macrophages.

Peritoneal macrophages were isolated as previously described (Sakashita et al. 2010. *J. Lipid Res.* 51:1263-1272), four days after injecting 1 ml of thioglycolate (TG) (3% wt/vol; Sigma Chemical Co.). Peritoneal leukocytes were isolated and incubated in 6-well culture dishes with 2 ml/well DMEM medium with 10% FBS at 37° C. for two hours. After washing with PBS two times, the firmly attached macrophages were used to measure ACAT1 mRNA and protein level.

Preparation of Mouse Aorta for En Face Analysis.

The en face procedure was performed as described (Drinane et al. 2009. *Circ. Res.* 104:337-345). Briefly, the animals were fasted overnight. The next day, blood was drawn and mice were euthanized and perfused with PBS. The innominate artery, carotid arteries, aortic arch, and descending aorta to the iliac bifurcation were surgically removed and fixed in 4% formalin. After staining with Sudan IV (which stains neutral lipid and is used routinely to reveal lesion areas), the lesion areas are quantified separately as total lesion area, the aortic arch (from the aortic valve to the left subclavian artery), thoracic aorta (from the left subclavian artery to the final intercostal arteries), and abdominal aorta (from the intercostal arteries to the bifurcation of the iliac arteries). Quantification of Sudan staining was performed using software Image J.

Plaque Cholesterol and Cholesterol Ester Content Measurement.

Mice were euthanized, and the descending aorta was removed for length and weight measurements. Lipids in these samples were then extracted by using chloroform:methanol at (2:1 v/v). After evaporation of organic solvents by nitrogen blowing at room temperature, lipid samples were re-dissolved in methanol for cholesterol measurements by using the Wako kit (Wako Diagnostics, Mountain View, Calif.). Cholesterol ester content was calculated by subtraction of total cholesterol value from the free cholesterol value.

Measurement of Blood Glucose, Insulin.

Blood glucose of mice fasted for 8 hours was measured by using a blood glucose meter with tip insertion from the tail veins. Blood Insulin, levels of mice fasted for 8 hours were measured by ELISA (Crystal Chem Inc., Downers Grove, Ill.) with a LUMINEX 200 machine (Millipore Corporation, Billerica, Mass.) as the readout.

Glucose and Insulin Tolerance Tests In Vivo.

Glucose tolerance tests, and insulin tolerance tests were based on methods described previously (Streeper et al. 2012. *Aging* (Albany N.Y.) 4:13-27). Briefly, for the glucose tolerance test, glucose levels in mice fasted for 8 hours (fasting started at 10 AM), were measured and used as basal blood glucose levels. Starved mice were subjected to peritoneal glucose injection (1.5 g/kg; Sigma Chemical Co., St. Louis, Mo.); blood glucose was monitored at 15, 30, 60, 90, and 120 minutes after injection. For insulin tolerance test, mice fasted for 2 hours (fasting started at 1 PM) were measured as values at 0 minute time point. After peritoneal insulin injection (0.75 mU/g, bovine pancreas insulin; Sigma Chemical Co., St. Louis. Mo.), blood glucose was monitored at 15, 30, 60, 90, and 120 minutes after insulin injection.

Stromal Vascular Cell Isolation.

The stromal vascular cell fraction (SVF) of white fat was isolated according to procedures previously described (Koliwad et al. 2010. *J. Clin. Invest.* 120:756-767). Briefly, epididymal adipose tissue of mice was excised and minced in DMEM/F12 (1:1) medium (Thermo Fisher Scientific, Waltham, Mass.) containing 1 mg/ml collagenase (type I; Worthington Biochemical, Worthington, Ohio) in a 37° C. water bath for 30 minutes with gentle shaking. Non-digested tissues including cell debris were filtered using a 40 µm nylon sieve; the filtrates containing SVF were centrifuged at 1,000 rpm (5 minutes) at room temperature to separate floating adipocytes. The non-adipocyte layers including SVF were collected and further centrifuged at 3,000 rpm for 5 minutes at room temperature. The SVF was washed one time with phosphate-buffered saline (PBS) containing 3% FBS and treated (10 minutes) with 1 ml red blood cell (RBC) lysis buffer (ebioscience, Cleveland, Ohio.) at room temperature for 10 minutes and washed again with PBS containing 3% FBS. After washing, cell suspension of SVF was used for flow analysis.

Measurement of ICAM and VCAM Expression in Primary Mouse Aortic Endothelial Cells.

The protocol used for isolating primary endothelial cells from aorta was modified from the procedure described in (Kobayashi et al. 2005. *Arterioscl. Thromb. Vasc. Biol.* 25:2114-2121). Briefly, aorta from Apoe$^{-/-}$ and DKO mice fed with Modified Paigen's diet for 12 weeks were removed and submerged in HBSS containing penicillin-streptomycin (1:100 dilution of 10,000 µg/ml stock solution (Cellgro, Herndon, Va.) and amphotericin B (1:100 250 µg/ml stock solution (Cellgro, Herndon, Va.). Adherent connective and fatty tissues were removed by dissection. Isolated mouse aortae were incubated in a sterile collagenase-elastase solution: collagenase type II (315 U/mL; Sigma Chemical Co., St. Louis, Mo.), elastase (1.25 U/mL; Sigma Chemical Co., St. Louis, Mo.) in HBSS at 37° C. for 10 minutes to remove the adventitia. The remaining media was chopped into small pieces. Media pieces were then incubated for another 30 minutes in collagenase I (2 mg/ml; Sigma Chemical Co., St. Louis, Mo.) solution at 37° C. The dissociated cell suspension was filtered with 40 µm filter to remove chunks of debris, followed by washing cells one time with PBS containing 3% FBS. The cell suspension was ready to stain with antibody for flow analysis.

Measurement of Leukocyte Migration into Atherosclerotic Plaque In Vivo.

Wild-type and Acat1$^{-M/-M}$ leukocytes were isolated from mouse blood based on procedures described previously (Huang et al. 2013. *Arterioscl. Thromb. Vasc. Biol.* 33:2081-2087), labeled with cell surface cross linking reagents that contain different fluorescent colors (PKH67GL, and PKH26GL; Sigma Chemical Co., St. Louis, Mo.) using the protocol supplied by the manufacturer, mixed with equal numbers of leukocytes from WT and Acat1$^{-M/-M}$ mice as a donor, and adoptive transfer was performed into Apoe$^{-/-}$ recipient mice with Modified Paigen's diet feeding for 4 weeks. After 16 hours, aortae were isolated and the percentage of infiltrated WT or Acat1$^{-M/-M}$ leukocytes inside aorta was examined by using flow cytometry.

Flow Cytometry.

Methods for cytometry analysis relating to blood and bone marrow studies were described previously (Huang et al. 2013. *Arterioscl. Thromb. Vasc. Biol.* 33:2081-2087). Cells from SVF were used to examine the cell surface antigens of macrophages including F4/80-APC (Biolegend, San Diego, Calif.), CD11b-FITC (Biolegend, San Diego, Calif.), and CD11c-PE (Biolegend, San Diego, Calif.). Cells isolated from mouse aorta were used to examine the expression levels of ICAM and VCAM in mouse aorta endothelium including ICAM-FITC (Biolegend, San Diego, Calif.), VCAM-PE (Biolegend, San Diego, Calif.), CD45-PerCP (Biolegend, San Diego, Calif.), and CD31-APC(Biolegend, San Diego, Calif.). Endothelial cell population is defined as CD31$^+$CD45$^-$. For Flow analysis, cells were stained with these antibodies at room temperature for 15 minutes and washed once with PBS containing 3% FBS. Flow cytometry analysis was performed using a BD FACSCANTO flow cytometry (BD Biosciences, San Jose, Calif.). Data were analyzed by using FlowJo Software (Tree Star, Ashland, Oreg.).

Example 2: MicroRNA-Mediated Inhibition of ACAT1 Expression

Artificial microRNA molecules were designed to target the 5' end of the coding sequence of mouse ACAT1 sequences listed in Table 3.

TABLE 3

| microRNA | ACAT1 Target Sequence | SEQ ID NO: |
|---|---|---|
| #52 | GGAGCTGAAGCCACTATTTAT | 9 |
| #53 | CTGTTTGAAGTGGACCACATCA | 10 |
| #54 | CCCGGTTCATTCTGATACTGGA | 11 |
| #55 | AACTACCCAAGGACTCCTACTGTA | 12 |

For example, the pre-microRNAs (including sense, antisense and loop regions) of microRNAs #54 and #55 were 5'-TGC TGT CCA GTA TCA GAA TGA ACC GGG TTT TGG CCA CTG ACT GAC CCG GTT CAC TGA TAC TGG A-3' (SEQ ID NO:13) and 5'-TGC TGT ACA GTA GGA GTC CTT GGG TAG TTT TGG CCA CTG ACT GAC TAC CCA AGC TCC TAC TGT A-3' (SEQ ID NO:14), respectively.

NIH-3T3 mouse fibroblasts were transiently transfected with one of several rAAV vectors encoding EmGFP and microRNA (miR) #52, #53, #54 or #55. Forty-eight hours post-transfection, GFP-positive cells were harvested by FACS. GFP-positive cells were washed then lysed in 10% SDS and syringe homogenized. Twenty microgram of protein per sample was subjected to SDS-PAGE. After western blot analysis, bands were quantified with ImageJ. ACAT1 intensity was normalized to GAPDH as a loading control and expressed as relative intensity. The results of this analysis are presented in Table 4.

TABLE 4

| Treatment | Relative Intensity |
|---|---|
| Mock Transfected | 1.00 |
| miR Negative Control | 1.02 |
| miR #52 | 0.77 |
| miR #53 | 0.56 |
| miR #54 | 0.54 |
| miR #55 | 0.39 |

This analysis indicated that microRNA molecules directed to mouse ACAT1 sequences could effectively decrease mouse ACAT1 gene expression by more than 50% compared to untreated controls.

Similarly, upon treatment of human HeLa cells or human MCF-7 cells with either of the microRNAs listed in Table 5 (10 nM concentration for two days) decreased human ACAT1 protein expression by 80%.

TABLE 5

| MicroRNA Sequence (5'->3') | SEQ ID NO: |
|---|---|
| CAUGAUCUUCCAGAUUGGAGUUCUA | 15 |
| UAGAACUCCAAUCUGGAAGAUCAUG | 16 |

Example 3: Effect of Recombinant Adeno-Associated Virus Expressing Acat1 siRNA Four different siRNA molecules (#52-#55; Table 3) targeting the mouse Acat1 gene were inserted into an endogenous mouse microRNA (miR) scaffold using Invitrogen's RNAi design tool. The artificial miRs were ligated into the mammalian expression vector pcDNA6.2-GW/EmGFP-miR. These Acat1miR constructs were tested along with a negative control (NC) miR (5'-TACTGCGCGTGGA-GACG-3'; SEQ ID NO:17), which does not match the sequence of any known vertebrate gene, in NIH-3T3 mouse fibroblasts. The miRs were delivered to the cells using a standard cDNA transfection protocol. The results showed that Acat1 miRs #54 and #55 were effective in causing 50-60% reduction in the ACAT1 protein content in treated mouse 3T3 fibroblasts.

MicroRNAs #54 and #55, and the NC miR molecule were also subcloned into a rAAV backbone vector (AAV-6P-SEWB) that contained the neuron-specific hSyn promoter (Sibley et al. 2012. Nucl. Acids Res. 40:9863-9875). This vector contained a strong nonspecific promoter that expressed Acat1 miRs in any cell type where the viral genome was expressed. For identification purposes, it also co-expressed GFP with the miRs. These three constructs were used to produce three recombinant AAV viruses. To test the efficacy and specificity of these viruses, cultured primary hippocampal neurons were treated with the NC AAV, or with AAV that expressed miR containing siRNA Acat1 #55. Two weeks after viral infection, the effects of AAVs on cholesteryl ester biosynthesis were tested in neurons. The results showed that the AAV harboring siRNA Acat1 #55 reduced cholesteryl ester biosynthesis by more than 50% ($P<0.01$), when compared with values in NC virus treated cells.

Example 4: Myeloid-Specific Acat1 Knockout Mouse

In order to study the role of ACAT1 in monocytes/macrophages, a mouse line with myeloid specific Acat1 knockout (Acat1$^{-M/-M}$) was produced. A homozygous conditional Acat1 mouse (Acat1$^{flox/flox}$) was prepared by constructing a targeting vector (Acat1$^{loxP}$) that contains a selectable marker cassette (Neo) flanked by loxP and flippase (Frt) sites. The loxP/Frt-flanked cassette was inserted into intron 13 of the mouse Acat1 gene. A third loxP-site was then placed upstream of exon 14 to generate the Acat1loxP transgene. Acat1 exon 14 includes amino acid His450 known to be essential for Acat1 enzymatic activity (Guo et al. 2005. J. Biol. Chem. 280:37814-37826). The construct was injected into ES cells; the correctly-targeted clones as determined by Southern blot and diagnostic PCR were injected into C57BL/6 blastocysts. Neo marker was removed by backcrossing with C57BL/6 Frt mice. Homozygous Acat1/LoxP allele (Acat1$^{flox/flox}$) were obtained and confirmed by diagnostic PCR. Additionally, Acat1$^{flox/flox}$ mice were crossed with lysozyme Cre$^{+/+}$ mice and two different lines were produced: Acat1$^{flox/flox}$/LysCre$^{+/+}$ (Acat1$^{-M/-M}$), and Acat1$^{flox/flox}$/LysCre$^{-/-}$ (Acat1$^{+M/+M}$).

Experiments were then performed to confirm that ACAT1 was specifically deleted in macrophages of the Acat1$^{-M/-M}$ mouse. Peritoneal macrophages were isolated from Acat1$^{-M/-M}$ and Acat1+$^{M/+M}$ mice four days after thioglycolate injection. The cells were incubated with aggregated LDL (agLDL), an agent known to provide large amount of cholesterol to macrophages (Khoo et al. 1988. Arteriosclerosis 8:348-358), with or without an ACAT inhibitor at a saturating concentration (Compound F12511; at 5 µM) (Chang et al. 2000. J. Biol. Chem. 275:28083-28092), for 16 hours, followed by $^3$H-oleate incorporation to measure the biosynthesis of labeled cholesteryl esters. The results showed that the cholesteryl ester synthesis rate in macrophages from the Acat1$^{-M/-M}$ mice was decreased by 90-95% when compared with the rate in macrophages from the Acat1+$^{M/+M}$ mice; the results of the control experiments showed that treating macrophages isolated from wild-type, or from LyzCre$^{+/+}$ mice, with the ACAT inhibitor (F12511) also drastically reduced the cholesteryl ester synthesis rate in these cells. Next, ACAT1 mRNA and protein content were measured in wild-type and Acat1$^{-M/-M}$ macrophages. The results showed that mRNA and protein expression in Acat1$^{-M/-M}$ macrophages was significantly decreased (by at least 80%). In wild-type mice, ACAT1 is abundantly expressed in the adrenal glands. A control experiment was also performed, which showed that the expression of ACAT1 in adrenal glands isolated from Acat1$^{-M/-M}$ mice was comparable to that of wild-type mice, demonstrating that ACAT1 is specifically inactivated in macrophages, but not in the adrenals, of Acat1$^{-M/-M}$ mice.

It was previously reported that global Acat1$^{-/-}$ mice contain higher numbers of monocytes (CD11b+), neutrophils (Gr1+), and B cells (CD19+), and slightly higher number of T cells (CD3+) in their blood when compared to wild-type littermates (Huang et al. 2013. Arterioscl. Thromb. Vasc. Biol. 33:2081-2087). When the number and type of leukocytes were examined in Acat1$^{-M/-M}$ mice, it was found that in contrast to global Acat1$^{-/-}$ mice, mice having no Acat1 expression in macrophages only (Acat1$^{-M/-M}$ mice) did not exhibit higher total leukocyte number in their blood when compared to wild-type mice. Further analysis of leukocyte composition showed that Acat1$^{-M/-M}$ mice have similar total numbers of myeloid and lymphoid cells in the blood as the wild-type mice. However, unlike global Acat1$^{-/-}$ mice, spleen size and lymph node cell numbers observed in Acat1$^{-M/-M}$ mice were comparable to values found in wild-type mice. Therefore, the phenotype of macrophage-specific Acat1 deletion is different from the global Acat1 deletion phenotype.

It also had shown previously that global Acat1$^{-/-}$ induces leukocytosis (Huang et al. 2013. Arterioscl. Thromb. Vasc. Biol. 33:2081-2087). Therefore, experiments were performed to compare the hematopoietic recovery of wild-type, global Acat1$^{-/-}$, and Acat1$^{-M/-M}$ mice after injection of the myelo-suppressive agent 5-fluorouracil (5-FU; 150 mg/kg) (Lindner et al. 1960. Cancer Res. 20:497-502). Mice from all three genotypes (7-9 weeks of age) were administered a single 5-FU injection. After injection, blood myeloid cells (CD11b+Gr1+) isolated from these mice were monitored by flow cytometry. Results showed that, on day 0 (before injection), global Acat1$^{-/-}$ mice, but not Acat1$^{-M/-M}$ mice, displayed higher numbers of blood myeloid cells as compared to wild-type mice. Six days post-injection, almost all of the myeloid cells in wild-type, Acat1$^{-/-}$ and Acat1$^{-M/-M}$ mice were depleted by 5-FU. Additionally, during the recovery phase (days 6-21 post injection), global Acat1$^{-/-}$ mice, but not Acat1$^{-M/-M}$ mice, consistently displayed an increase in myeloid cells when compared to wild-type mice. These results indicated that total Acat1$^{-/-}$, but not macrophage-targeted ACAT1 deletion (Acat1$^{-M/-M}$), boosted myeloid cell proliferation in bone marrow. These data again support the conclusion that macrophage-targeted Acat1 deletion produces a unique phenotype.

In addition to having no affect on bone marrow, the Acat1$^{-M/-M}$ mouse did not exhibit dry eye syndrome, as is observed in the global Acat1$^{-/-}$ mouse (Yagyu et al. 2000. *J. Biol. Chem.* 275:21324-30). In addition, unlike the global Acat1$^{-/-}$ mouse, the Acat1$^{-M/-M}$ mouse does not exhibit abnormalities in any of the following parameters: composition of the hematopoietic stem cells or the proliferation rate of these cells, blood leukocyte compositions and spleen weight, or bone marrow cell expression of interleukin 3 and 7 receptors. Thus, these results demonstrate that the Acat1$^{-M/-M}$ mouse is a better model than the global Acat1$^{-/-}$ mouse to delineate the specific functions of Acat1 in macrophage cells in atherosclerosis.

Moreover, unlike global Acat1 knockout (KO) mice, Acat1$^{-M/-M}$ knockout in mice does not cause leukocytosis or overt abnormalities. Surprisingly, when compared to wild-type (WT) mice, the Acat1$^{-M/-M}$ mice, but not global Acat1 KO mice, exhibited resistance to high fat diet-induced obesity. These data indicate that ACAT1 activity in myeloids cells specifically is a target that can be exploited for anti-obesity treatments. When Acat1$^{-M/-M}$ mice were fed a typical laboratory chow diet or a high fat diet, both groups of Acat1$^{-M/-M}$ mice exhibited increased insulin sensitivity, fewer infiltrating macrophages in adipose tissue, and smaller fat cells. The different diets also produced differential responses in the Acat1$^{-M/-M}$ mice. For example, the Acat1$^{-M/-M}$ mice fed normal laboratory chow exhibited lower circulating levels of leptin and other adipocytokines in blood, while Acat1$^{-M/-M}$ mice fed a high fat diet exhibited slower migration of monocytes to chronically inflamed adipose tissue. These data clearly show that ACAT1 activity in macrophages can be exploited as a new therapeutic target to prevent and/or treat diet-induced obesity.

Example 5: Role of ACAT1 in Metabolic Syndrome and Coronary Artery Disease (Atherosclerosis)

With respect to treatment of one of the central co-morbidities associated with metabolic syndrome, atherosclerosis, there has been some inconsistency in the studies performed to date. Experiments with different ACAT inhibitors have suggested a role for ACAT1 in atherosclerosis progression, with both ACAT1 and ACAT2 inhibitors having efficacy in different animal studies. Also, it has been found that loss of Acat1 gene expression increased the number of leukocytes in blood (Huang et al. 2013. *Arterioscler. Thromb. Vasc. Biol.* 33:2081-2087). It is known that leukocytes, which include monocytes, macrophages, B cells, and T cells, participate in different stages of atherosclerosis. These data collected in global Acat1$^{-/-}$ mice (knockout of the gene in all cells) are not capable of identifying a specific role for macrophages, or any other cell type, as being critical to progression of atherosclerosis. Therefore, these early studies did not specifically identify knockout of Acat1 in macrophages as being critical to atherosclerosis pathogenesis. Thus, to resolve the inconsistency in results between ACAT inhibitor studies and global Acat1$^{-/-}$ mouse studies, the conditional Acat1$^{-M/-M}$ mouse line was used to examine the effects of macrophage-specific Acat1$^{-/-}$ in the atherosclerotic Apoe$^{-/-}$ mouse model.

Acat1$^{-M/-M}$ mice were crossed with Apoe$^{-/-}$ mice (an established mouse model for studying atherosclerosis) to generate the Acat1$^{-M/-M}$/Apoe$^{-/-}$ mice (denoted DKO mice). Age-matched DKO mice and control Apoe$^{-/-}$ mice were fed with Modified Paigen's diet for 12 weeks. After 12 weeks, the mice were sacrificed, and aortae were isolated, stained with Sudan IV, and cut longitudinally for en face analysis. The results showed that the percentage of atherosclerotic lesions (total area) was significantly decreased in DKO mice when compared with values in the control mice (Apoe$^{-/-}$)(5% versus 18%). Additional analyses showed that Acat1$^{-M/-M}$ phenotype also was associated with a significant decrease in percentage of atherosclerotic lesions in various regions of the aorta (aortic arch, thoracic aorta, and abdominal aorta). In control experiments where mice were fed normal chow diet for 16 weeks instead of the Modified Paigen's diet, atherosclerotic lesion areas were present in both the Apoe$^{-/-}$ and the DKO mice, but DKO mice still exhibited significantly less plaque areas than the Apoe$^{-/-}$ mice. These results demonstrated that Acat1 deletion/ablation specifically in macrophages reduces atherosclerotic plaque formation in vivo, identifying macrophage-specific ACAT1 inhibition as a treatment for atherosclerosis, which is a co-morbidity of metabolic syndrome.

To further examine the effect of macrophage-specific Acat1 gene ablation on atherogenesis, levels of cholesterol in plaques was investigated. Descending aortae were isolated from Apoe$^{-/-}$ and DKO mice fed with Modified Paigen's diet for 12 weeks, and total cholesterol and cholesteryl ester values were measured. The results showed that in DKO mice, the total cholesterol level and the cholesterol ester levels in descending plaques were significantly reduced (by 60% for total cholesterol or by 95% for cholesteryl esters) when compared with values in the Apoe$^{-/-}$ mice. These data also confirm the beneficial phenotype of depleting macrophage-specific ACAT1 in atherogenesis.

In 2007, two groups independently reported that Ly6C$^{hi}$ monocyte subset is the major cell population among various monocyte subsets responsible for migrating into intima region of aorta to develop the atherosclerotic plaques (Tacke et al. 2007. *J. Clin. Invest.* 117:185-194; Swirski et al. 2007. *J. Clin. Invest.* 117:195-205). These two groups showed that the number of Ly6C$^{hi}$ monocytes is increased in Apoe$^{-/-}$ mouse blood, and is recruited to bind to activated endothelium, followed by infiltration into lesional areas. The results suggested that DKO mice might contain fewer foamy macrophages; i.e., Acat1$^{-M/-M}$ may retard macrophage infiltration into the lesion area. Therefore, experiments were performed to assess some of the key steps involved in Ly6C$^{hi}$ monocyte recruitment and entry into lesions during atherosclerosis development. First, Ly6C$^{hi}$ monocytes were isolated from wild-type and Acat1$^{-M/-M}$ mouse blood and expression levels of several activated cell surface markers, including CD49, CD62L, CD29, CD11c, and CD11b, were quantified by flow cytometry. The results showed that the total number of Ly6C$^{hi}$ monocytes in blood is similar in wild-type and Acat1$^{-M/-M}$ mice. However, when expression levels of activation markers were analyzed, there were differences in wild-type versus Acat1$^{-M/-M}$ mice. On Ly6C$^{hi}$ monocytes expression of CD49d and CD62L were decreased in Acat1$^{-M/-M}$ mice as compared to wild-type mice, while expression levels of the other cell surface activation markers (CD11c and CD11b) remained the same between these two mice strains.

It is known that expression levels of key adhesion molecules on vascular endothelium, e.g., intercellular adhesion molecule-1 (ICAM-1) and vascular cell adhesion molecule-1 (VCAM-1), are increased in hypercholesterolemia (Nakashima et al. 1998. *Arterioscl. Thromb. Vasc. Biol.* 18:842-851). Therefore, experiments were performed to determine if ICAM-1 and/or VCAM-1 expression levels are altered in Acat1$^{-M/-M}$ mice. Single suspended cells from mouse aorta were isolated from age matched Apoe$^{-/-}$ and DKO mice after modified Paigen's diet feeding for 12 weeks. The CD45 negative and CD31 positive population was defined as a vascular endothelial population; from this population, the expression levels of ICAM-1 and VCAM-1 were determined. The results showed that VCAM-1 expression in DKO mouse endothelial cells was decreased significantly when compared to Apoe$^{-/-}$ control mice.

It also is known that VCAM-1 in vascular endothelial cells is a key receptor for CD49d present in monocytes/macrophages; the interactions between VCAM-1 and CD49d are known to play an important role in binding of leukocytes to activated endothelial cells during the process of leukocyte extravasation at inflammatory sites, as reviewed in (Galkina, E. and K. Ley. 2007. *Current Drug Targ.* 8:1239-1248). Therefore, experiments were performed to determine whether Acat1$^{-M/-M}$ directly decreases expression of CD49d on Ly6C$^{hi}$ monocyte, and indirectly decreases expression of VCAM-1 on vascular endothelium; these two effects act synergistically to retard monocyte recruitment into lesion areas and cause reduction in atherosclerotic plague. First, an in vivo leukocyte migration assay was performed to measure how many exogenously labeled leukocytes migrate into aorta during the adopted transfer process (Shah et al. 2011. *Circulation* 124:2338-2349). The results showed that, when compared to wild-type leukocytes, there were significantly fewer Acat1$^{-M/-M}$ leukocytes infiltrating into aorta. The results from the in vivo leukocyte migration assay indicated that Acat1$^{-M/-M}$ slows down leukocyte migration into atherosclerotic endothelium. These data in macrophage-specific Acat1 ablation mice showed that the Acat1$^{-M/-M}$ phenotype was beneficial to the development of atherosclerosis. These data, therefore, provide support for a role of ACAT1 inhibition as a method of preventing and/or treating metabolic syndrome, specifically the co-morbidity of coronary artery disease (atherosclerosis).

Further experiments relevant to treatment of metabolic syndrome were performed with the Acat$^{-M/-M}$ mouse model, specifically to examine the link of Acat1 activity with markers of type II diabetes. Experiments were performed to determine if Acat1$^{-M/-M}$ genotype has a beneficial effect on insulin sensitivity in Apoe$^{-/-}$ mice. Age and sex matched Apoe$^{-/-}$ and DKO mice were fed standard laboratory chow or Modified Paigen's diet for 6-16 weeks. The results showed that, when mice were fed the standard laboratory chow diet, there was no significant difference in fasting blood glucose levels between the Apoe$^{-/-}$ and DKO mice. Fasting glucose levels tended to be lower in female DKO mice as compared to the values in female Apoe$^{-/-}$ mice; however, the values in these mice fluctuate among different time periods studied, and the differences between these two strains were not consistently observed during the study period (6-16 weeks). In contrast, under Modified Paigen's diet, both male and female DKO mice had lower fasting glucose levels than the Apoe$^{-/-}$ mice. When male mice only were fed with Modified Paigen's diet, fasting insulin levels in the DKO mice were significantly lower than levels observed in Apoe$^{-/-}$ mice. These differences in the macrophage-specific Acat1 ablated mice again support a role for Acat1 inhibition as a treatment strategy for metabolic syndrome.

Based on the results described above, the results support a link between macrophage-specific Acat1 inhibition and improved glucose tolerance. Experiments were performed to examine glucose tolerance by measuring blood glucose levels at various time points after injection of glucose at high doses (i.p) in DKO and Apoe$^{-/-}$ mice. The results showed that blood glucose levels were increased in both male and female Apoe$^{-/-}$ and DKO mice 15 minutes after glucose injection, but the glucose levels in the DKO mice were significantly lower than the levels in Apoe$^{-/-}$ mice. For both male and female mice, the area under the blood glucose response curve (AUC) for DKO mice was significantly less than the AUC for Apoe$^{-/-}$ mice. Next, insulin tolerance tests were performed in these two mice strains. After starving for 2 hours, male Apoe$^{-/-}$ and DKO mice fed with Modified Paigen's diet were injected with insulin (i.p.), and blood glucose levels were monitored. The results showed that blood glucose levels in DKO mice dropped significantly faster than levels in Apoe$^{-/-}$ mice. Additionally, unlike Apoe$^{-/-}$ mice, the glucose levels in DKO mice remained low during the recovery phase. These results showed that, based on insulin tolerance testing, DKO mice exhibited enhanced insulin tolerance upon glucose stimulation, again providing support for the role of Acat1 inhibition as a treatment for metabolic syndrome.

The results described above indicated that DKO mice respond better to acute glucose challenge and clear glucose from the blood more efficiently. To determine whether insulin secretion of DKO mice is abnormal, insulin levels were examined in male Apoe$^{-/-}$ and DKO mice during the glucose tolerance tests. Upon glucose injection, the highly elevated blood insulin levels observed were very similar between Apoe$^{-/-}$ and DKO mice, indicating that insulin secretion is likely intact, and not abnormal in this mouse model.

Subsequently, body weights of Apoe$^{-/-}$ and DKO mice fed standard laboratory chow or Modified Paigen's diet were examined for up to 16 weeks. The results showed that there was no significant difference in body weights between Apoe$^{-/-}$ mice and DKO mice (male and female) fed standard diets. However, when fed Modified Paigen's diet, both male and female DKO mice gained more weight as compared to Apoe$^{-/-}$ mice. Food intake was also monitored during the same experiment, the results showed there was no significant difference in food consumption levels, indicating the differences in body weight (body weight phenotype) were not due simply to less food intake. Staining of subcutaneous areas isolated from age matched Apoe$^{-/-}$ and DKO mice fed with Modified Paigen's diet for 12 weeks was also performed. The results showed that under Apoe$^{-/-}$ background, Acat1$^{-M/-M}$ caused large accumulation of immune cells and cholesterol crystal deposits within the subcutaneous area. The same method was used to examine the subcutaneous area isolated from Apoe$^{-/-}$ mice and the DKO mice fed with standard laboratory chow diet or with Modified Paigen's diet. The results showed that this novel phenotype only occurred when the DKO mice were fed with Modified Paigen's diet. A similar phenotype had been reported previously in mice with total Acat1 gene deletion under Apoe$^{-/-}$ background (Accad et al. 2000. *J. Clin. Invest.* 105:711-719). Results of additional control experiments showed that the novel phenotype (i.e., cholesterol crystal deposits within the subcutaneous area) only occurred in Acat1$^{-M/-M/}$ Apoe$^{-/-}$ mice fed with Modified Paigen's diet. This phenotype was absent in Acat1$^{-M/-M}$Apoe$^{+/+}$ mice fed with Modified Paigen's diet. Thus, Acat1$^{-M/-M}$ mice with normal apoE function do not produce this novel phenotype. These results indicate that inhibiting ACAT1 activity, or depleting ACAT1 protein in macrophages, can be beneficial in the treatment of obesity, metabolic syndrome, and atherosclerosis as long as the patient contains normal apoE function. It is important to point out that humans lacking apoE are extremely rare in the human population (in the order of 1 in one million).

In exploring the mechanisms responsible for the beneficial phenotype caused by Acat1$^{-M/-M}$ in Apoe$^{-/-}$ mouse, it has also been shown that there are multiple ways to reduce plaque formation when Acat1 gene is silent in macrophages. Data suggested that Acat1$^{-M/-M}$ might affect the functionality of lipid rafts on Ly6C$^{hi}$ monocytes, which in turn lead to decreased expression of CD49d and CD62L. Data also suggested that Acat1$^{-M/-M}$ could affect transcription levels of those activation markers. Increasing evidence shows that the vascular endothelium is sensitive to changes in blood glucose concentrations. For example, a study in rats has shown that hyperglycemia promoted expression of VCAM-1 on vascular endothelium, leading to leukocyte adhesion, the initial step in atherosclerosis (Booth et al. 2002. *Diabetes* 51:1556-1564; Azcutia et al. 2010. PLOS One 5:e10091). It has now been shown that an Acat1$^{-M/-M}$ under Apoe$^{-/-}$ phenotype in vivo in mice is associated with lower steady state glucose and insulin levels in blood, improved glucose and insulin tolerance, and improved insulin sensitivity. Thus, lower steady state blood glucose may be responsible for the decreased VCAM-1 expression in Acat1$^{-M/-M}$ mice.

Example 6: Role of ACAT1 in Adipose Tissue and Insulin Sensitivity

Weight gain in male wild-type mice and Acat1$^{-M/-M}$ mice fed with chow or Western diet was monitored at 8 weeks of age. The results showed that, under chow diet for up to 20 weeks, there was no significant difference in body weight, or in fasting glucose levels between the two genotypes. In contrast, under Western diet for up to 16 weeks, Acat1$^{-M/-M}$ mice gained less weight (by up to 15%) as compared to wild-type mice. In wild-type mice, Western diet feeding for 8-10 weeks increased the fasting blood glucose level significantly; such increase was much smaller in the Acat1$^{-M/-M}$ mice. Unlike Acat1$^{-M/-M}$, Western diet caused the global Acat1$^{-/-}$ mice to gain more weight (by up to 35%) and to have elevated fasting blood glucose levels as compared to wild-type mice (by up to 68%). To determine the whole body lean and fat mass, wild-type and Acat1$^{-M/-M}$ mice fed with chow diet for 10 weeks, or Western diet for 10 or 16 weeks were analyzed by $^{1}$H-MRS. The results showed that on chow diet, no detectable difference existed between wild-type and Acat1$^{-M/-M}$ mice in their body composition. Following Western diet for 10 or 16 weeks, the Acat1$^{-M/-M}$ mice and wild-type mice showed comparable amount of lean mass, but Acat1$^{-M/-M}$ mice showed significantly less fat mass than the wild-type mice (by 37% in 10 weeks or 15% in 16 weeks), demonstrating that the lower body weight is largely due to reduced adiposity in these mice.

Glucose tolerance tests were also performed in male wild-type and Acat1$^{-M/-M}$ mice fed with Western diet for 10 weeks. These data showed that following i.p. injection of glucose, blood glucose levels in Acat1$^{-M/-M}$ mice were significantly lower as compared to those in the wild-type mice. Similar results were found in female mice. Area under the curve (AUC) of blood glucose levels was significantly smaller in male and female Acat1$^{-M/-M}$ mice than those of the wild-type mice, suggesting that Acat1$^{-M/-M}$ mice have improved glucose tolerance under Western diet. The chow-fed Acat1 Acat1$^{-M/-M}$ mice had a trend toward decreased fasting blood insulin levels. Following 8 weeks of Western diet, the fasting blood insulin levels in the Acat1$^{-M/-M}$ mice were significantly lower (by more than 50%) than wild-type mice. After fasting and re-feeding, both genotypes had large increases in blood insulin levels to a comparable level, suggesting that the insulin secretion capacity by pancreatic β-cells was not affected by Acat1$^{-M/-M}$. Together, these results show that Acat1$^{-M/-M}$ improves blood glucose tolerance and insulin sensitivity.

Hyperinsulinemic-euglycemic clamp was performed in male wild-type and Acat1$^{-M/-M}$ mice fed with chow or Western diet for 10 weeks. The results showed that on both diets, the Acat1$^{-M/-M}$ mice exhibited higher glucose infusion rates during clamps than the wild-type mice, indicating that the Acat1$^{-M/-M}$ mice were more insulin sensitive than wild-type mice during hyperinsulinemic-euglycemic clamp analysis. Insulin-stimulated whole body glucose turnover rates were significantly higher in the Acat1$^{-M/-M}$ mice; whole body glycolysis rates tended to be higher in Acat1$^{-M/-M}$ mice, but whole body glycogen synthesis rates did not differ between these two genotypes. Results of basal hepatic glucose production (HGP) rates showed no significant difference between the two genotypes on chow; however, following Western diet, basal HGP rates were lower in Acat1$^{-M/-M}$ mice, which was consistent with lower fasting glucose levels in these mice. Hepatic insulin action (insulin-mediated percent suppression of basal HGP) between these two genotypes was comparable, indicating that Acat1$^{-M/-M}$ may not affect diet-induced insulin resistance in the liver. Insulin-stimulated glucose uptake in individual organs was measured by using [$^{14}$C] 2-deoxyglucose injection during clamps. The results showed that on chow diet, insulin-stimulated glucose uptake in skeletal muscle was significantly elevated in the Acat1$^{-M/-M}$ mice. Following Western diet for 10 weeks, insulin-stimulated glucose uptake in brown adipose tissue was significantly elevated in the Acat1$^{-M/-M}$ mice. These studies support the conclusion that Acat1$^{-M/-M}$ mice display increased insulin sensitivity and glucose metabolism in peripheral organs in vivo.

It was subsequently determined whether Acat1$^{-M/-M}$ also affects adipocyte cell size. Gonadal fat pads from the wild-type and Acat1$^{-M/-M}$ mice on chow or Western diet for 8 weeks were isolated and adipocyte size was measured. The results showed that, on both chow and Western diet, the adipocyte size in Acat1$^{-M/-M}$ mice was significantly decreased (Chow diet: wild-type mean=2971, Acat1$^{-M/-M}$ mean=1712; wild-type median=2971, Acat1$^{-M/-M}$ median=1558) (Western diet: wild-type mean=5449, Acat1$^{-M/-M}$ mean=3577; wild-type median=4956, Acat1$^{-M/-M}$ median=3292). When fed with Western diet, Acat1$^{-M/-M}$ mice contained significantly less crown-like structure (CLS) in gonadal fat pads than that in wild-type mice (by about 50%), suggesting that Acat1$^{-M/-M}$ decreased the adipose tissue macrophage (ATM) number. To validate this interpretation, stromal vascular fraction (SVF) from gonadal fat pads of wild-type and Acat1$^{-M/-M}$ mice on chow or Western diet for 8 weeks were analyzed by flow cytometry. The results showed that Acat1$^{-M/-M}$ mice contained significantly fewer macrophages than wild-type mice (by 75% based on macrophage number per adipose tissue weight, or by 55% based on % macrophages of SVF cells) under chow and Western diet. ATM polarization was examined by flow cytometry. On chow diet, ATM polarization between these two genotypes was similar. On Western diet, in wild-type mice, 42% ATM was M1, 24% was M2-like phenotype, while in Acat1$^{-M/-M}$ mice, 22% ATM was M1, 46% was M2-like phenotype. The M2/M1 ratio of ATMs was greatly increased in Acat1$^{-M/-M}$ mice on Western diet. These results were confirmed by using two other M2 markers. To summarize, on chow diet, Acat1$^{-M/-M}$ decreased the ATM content without affecting its M2/M1 ratio; on Western diet, Acat1$^{-M/-M}$ decreased the ATM content and increased the M2/M1 ratio of ATMs.

Indirect calorimetry studies were performed using metabolic cages (TSE Systems, Midland, Mich.) in male wild-type and Acat1$^{-M/-M}$ mice on chow diet for 10 weeks or on Western diet for 16 weeks. The results showed that on either diet, daily food intake between the two genotypes was not significantly different. On chow diet, energy expenditure rates were markedly elevated in the Acat1$^{-M/-M}$ mice. However, on Western diet, there were no differences between the two strains. The results presented herein showed that the Acat1$^{-M/-M}$ mice on Western diet for longer than 8 weeks exhibited rapid weight gain in a manner similar to the wild-type mice. In the present experiment, the prolonged time on Western diet (16 week) may have eliminated the difference in energy expenditure between the two strains. Subsequently, the two mouse strains were placed on chow or Western diet for only 8 weeks, and the expression of the key thermogenesis gene Ucp1 (that encodes the mitochondrial uncoupling protein 1) in white adipose tissue (WAT) and brown adipose tissue (BAT) was monitored in these mice. The expression of the gene that encodes the key protein for mitochondrial electron transport chain cytochrome C (Cytc) was also monitored. The results showed that WAT in Acat1$^{-M/-M}$ mice on both diets displayed higher Ucp1 expression than that of wild-type mice. The Ucp1 expression level was also elevated in BAT isolated from Acat1$^{-M/-M}$ mice on Western diet, but not on chow diet. No difference in Cytc expression in WAT or BAT from these two strains under chow or Western was observed. These results indicate that beiging effects may play a key role in higher energy expenditure rates in Acat1$^{-M/-M}$ mice.

The results presented herein indicated that there were fewer ATMs present in the Acat1$^{-M/-M}$ mice. It is possible that Acat1$^{-M/-M}$ retards monocytes/macrophages to migrate to adipose tissue in vivo. Therefore, using a method known in the art (Oh et al. 2012. *Diabetes* 61:346-354), it was determined whether macrophage migration was affected. Monocytes isolated from chow-fed wild-type or Acat1$^{-M/-M}$ mice were used as donors; wild-type mice on chow diet or on Western diet for 2 or 8 weeks as indicated were used as the recipients. The results showed that, with chow-fed wild-type mice as recipients, about 0.3% of total cells in SVF could be attributed to donor monocytes, and no difference was detected between the two donors. When 2-week Western diet-fed wild-type mice were used as recipients, % donor monocytes present in SVF increased in both donor cells; % Acat1$^{-M/-M}$ donor monocytes had a trend to be less than % wild-type donor monocytes, but the difference was not statistically significant. When 8-week Western diet-fed wild-type mice were used as recipients, % donor monocytes present in SVF increased even higher for both donors; under this condition, % Acat1$^{-M/-M}$ donor was significantly less than % wild-type donor. These results indicated that Acat1$^{-M/-M}$ affects monocytes/macrophages migration to inflamed adipose tissue less efficiently than the wild-type. To further validate the observation, the expression of Ly6C$^{hi}$ monocyte adhesion molecules, which adhere to endothelium to initiate the infiltration, was examined as was the expression of their receptors expressed on the endothelium, i.e., intercellular adhesion molecule-1 (ICAM-1) and vascular cell adhesion molecule-1 (VCAM-1). Ly6C$^{hi}$ monocytes were isolated from the blood of chow and Western-fed wild-type and Acat1$^{-M/-M}$. Cell surface expressions of CD29, CD49d, CD62L, CD11c, and CD11b were quantified by flow cytometry. The result showed that the % of Ly6C$^{hi}$ monocytes between these two genotypes was the same on chow, but decreased in Acat1$^{-M/-M}$ mice on Western diet. The expressions of CD49d and CD62L were decreased in Acat1$^{-M/-M}$ monocytes on both chow and Western diet as compared to wild-type; and CD29 was only decreased in Acat1$^{-M/-M}$ monocytes on Western diet. The expression of CD11c and CD11b remained the same between these two genotypes.

Endothelial cells express ICAM-1 and VCAM-1 that recognize the adhesion molecules on the cell surface of monocytes. Mouse aortic endothelial cells were isolated and the expressions of ICAM-1 and VCAM-1 were examined. The results showed that on Western diet, the ICAM-1 and VCAM-1 expression levels in the endothelial cells from Acat1$^{-M/-M}$ mice were decreased when compared to those from wild-type, while on chow diet, there was no significant difference between those two genotypes. Together, these results show that Acat1$^{-M/-M}$ decreases the expression of CD49d, CD29, and CD62L on Ly6C$^{hi}$ monocytes, and indirectly decreases the expressions of ICAM-1 and VCAM-1 on endothelium on Western diet.

Retarded Acat1$^{-M/-M}$ monocyte migration may compromise immune response upon acute virus injection. Therefore, it was determined whether immune responses to vaccinia virus (VV-WR strain) were affected in the Acat1$^{-M/-M}$ mouse. The result showed that ten days after virus infection, the viral titers and the titers of serum antibodies neutralizing VV-WR were very similar between these two genotypes, suggesting that Acat1 deletion in monocytes/macrophages does not compromise systemic immunity upon acute virus infection.

What is claimed is:

1. A method for treating diet-induced obesity in a subject comprising contacting myeloid cells of a subject with a Acyl-CoA:Cholesterol Acyltransferase 1 (ACAT1)-selective inhibitor, wherein the ACAT1-selective inhibitor exhibits an $IC_{50}$ value that is at least two-fold lower than the corresponding $IC_{50}$ value for ACAT2, thereby treating diet-induced obesity in the subject.

2. The method of claim 1, wherein contacting myeloid cells of a subject with a Acyl-CoA: Cholesterol Acyltransferase 1-selective inhibitor increases insulin sensitivity, lowers circulating levels of adipocytokines, decreases numbers of infiltrating macrophages in adipose tissue and/or decreases fat cell size.

3. The method of claim 1, wherein the inhibitor inhibits the expression or activity of Acyl-CoA: Cholesterol Acyltransferase 1.

4. The method of claim 1, wherein the Acyl-CoA:Cholesterol Acyltransferase 1-selective inhibitor is formulated in a liposome, nanoparticle or exosome.

5. The method of claim 4, wherein the liposome, nanoparticle or exosome is modified with a moiety to target macrophages.

* * * * *